US010022068B2

United States Patent
McGonigle et al.

(10) Patent No.: US 10,022,068 B2
(45) Date of Patent: Jul. 17, 2018

(54) SYSTEMS AND METHODS FOR DETECTING HELD BREATH EVENTS

(71) Applicant: Covidien LP, Mansfield, MA (US)

(72) Inventors: Scott McGonigle, Edinburgh (GB); James Ochs, Seattle, WA (US)

(73) Assignee: Covidien LP, Mansfield, MA (US)

( * ) Notice: Subject to any disclaimer, the term of this patent is extended or adjusted under 35 U.S.C. 154(b) by 543 days.

(21) Appl. No.: 14/524,327

(22) Filed: Oct. 27, 2014

(65) Prior Publication Data

US 2015/0119720 A1 Apr. 30, 2015

Related U.S. Application Data

(60) Provisional application No. 61/896,538, filed on Oct. 28, 2013.

(51) Int. Cl.
*A61B 5/08* (2006.01)
*A61B 5/00* (2006.01)

(52) U.S. Cl.
CPC .......... *A61B 5/0806* (2013.01); *A61B 5/0077* (2013.01); *A61B 5/0816* (2013.01); *A61B 5/7278* (2013.01)

(58) Field of Classification Search
None
See application file for complete search history.

(56) References Cited

U.S. PATENT DOCUMENTS

| | | | |
|---|---|---|---|
| 3,532,087 A | 10/1970 | Horn | |
| 3,678,296 A | 7/1972 | Day | |
| 3,884,219 A | 5/1975 | Richardson | |
| 3,926,177 A | 12/1975 | Hardway | |
| 3,976,052 A | 8/1976 | Junginger | |
| 4,289,141 A | 9/1981 | Cormier | |
| 4,621,643 A | 11/1986 | New | |
| 4,696,307 A | 9/1987 | Montgieux | |
| 5,143,078 A | 9/1992 | Mather | |
| 5,188,108 A | 2/1993 | Secker | |
| 5,273,036 A | 12/1993 | Kronberg | |
| 5,279,296 A | 1/1994 | Thurston | |
| 5,285,783 A | 2/1994 | Secker | |
| 5,285,784 A | 2/1994 | Secker | |
| 5,368,026 A | 11/1994 | Swedlow | |

(Continued)

FOREIGN PATENT DOCUMENTS

| | | |
|---|---|---|
| EP | 0072601 | 7/1986 |
| EP | 1344488 | 9/2004 |

(Continued)

OTHER PUBLICATIONS

Karmakar et al., Detection of Respiratory Arousals Using Photoplethysmography (PPG) Signal in Sleep Apnea Patients, IEEE Journal of Biomedical and Health Informatics, vol. 18, No. 3, May 2014.*

(Continued)

*Primary Examiner* — Katherine Fernandez
*Assistant Examiner* — Bradley Impink

(57) ABSTRACT

Systems and methods are provided for detecting held breath events. A physiological signal, such as a photoplethysmograph (PPG) signal, is processed to extract respiration-related morphology metric signals. The morphology signals are analyzed to determine when a patient's breath is being held.

17 Claims, 7 Drawing Sheets

(56) References Cited

U.S. PATENT DOCUMENTS

| | | |
|---|---|---|
| 5,398,682 A | 3/1995 | Lynn |
| 5,439,483 A | 8/1995 | Duong-Van |
| 5,482,036 A | 1/1996 | Diab |
| 5,490,505 A | 2/1996 | Diab |
| 5,558,096 A | 9/1996 | Palatnik |
| 5,575,284 A | 11/1996 | Athan |
| 5,584,295 A | 12/1996 | Muller |
| 5,588,425 A | 12/1996 | Sackner |
| 5,590,650 A | 1/1997 | Genova |
| 5,605,151 A | 2/1997 | Lynn |
| 5,632,272 A | 5/1997 | Diab |
| 5,680,871 A | 10/1997 | Ganshorn |
| 5,682,898 A | 11/1997 | Aung |
| 5,685,299 A | 11/1997 | Diab |
| 5,769,785 A | 6/1998 | Diab |
| 5,778,881 A | 7/1998 | Sun |
| 5,795,304 A | 8/1998 | Sun |
| 5,797,840 A | 8/1998 | Akselrod |
| 5,827,195 A | 10/1998 | Lander |
| 5,862,805 A | 1/1999 | Nitzan |
| 5,865,736 A | 2/1999 | Baker |
| 5,891,023 A | 4/1999 | Lynn |
| 5,919,133 A | 7/1999 | Taylor |
| 5,924,980 A | 7/1999 | Coetzee |
| 5,967,995 A | 10/1999 | Shusterman |
| 6,002,952 A | 12/1999 | Diab |
| 6,018,673 A | 1/2000 | Chin |
| 6,035,223 A | 3/2000 | Baker |
| 6,036,642 A | 3/2000 | Diab |
| 6,036,653 A | 3/2000 | Baba |
| 6,081,742 A | 6/2000 | Amano |
| 6,094,592 A | 7/2000 | Yorkey |
| 6,095,984 A | 8/2000 | Amano |
| 6,117,075 A | 9/2000 | Barnea |
| 6,129,675 A | 10/2000 | Jay |
| 6,135,952 A | 10/2000 | Coetzee |
| 6,135,966 A | 10/2000 | Ko |
| 6,142,953 A | 11/2000 | Burton |
| 6,144,867 A | 11/2000 | Walker |
| 6,171,257 B1 | 1/2001 | Wei |
| 6,171,258 B1 | 1/2001 | Karakasoglu |
| 6,178,261 B1 | 1/2001 | Williams |
| 6,206,830 B1 | 3/2001 | Diab |
| 6,208,951 B1 | 3/2001 | Kumar |
| 6,223,064 B1 | 4/2001 | Lynn |
| 6,229,856 B1 | 5/2001 | Diab |
| 6,238,351 B1 | 5/2001 | Orr |
| 6,263,222 B1 | 7/2001 | Diab |
| 6,266,547 B1 | 7/2001 | Walker |
| 6,293,915 B1 | 9/2001 | Amano |
| 6,306,088 B1 | 10/2001 | Krausman |
| 6,325,761 B1 | 12/2001 | Jay |
| 6,331,162 B1 * | 12/2001 | Mitchell ............ A61B 5/02125 600/485 |
| 6,334,065 B1 | 12/2001 | Al-Ali |
| 6,342,039 B1 | 1/2002 | Lynn |
| 6,350,242 B1 | 2/2002 | Doten |
| 6,361,501 B1 | 3/2002 | Amano |
| 6,393,311 B1 | 5/2002 | Reuben |
| 6,398,727 B1 | 6/2002 | Bui |
| 6,405,076 B1 | 6/2002 | Taylor |
| 6,408,198 B1 | 6/2002 | Hanna |
| 6,434,408 B1 | 8/2002 | Heckel |
| 6,436,038 B1 | 8/2002 | Engstrom |
| 6,463,311 B1 | 10/2002 | Diab |
| 6,501,975 B2 | 12/2002 | Diab |
| 6,506,153 B1 | 1/2003 | Littek |
| 6,546,267 B1 | 4/2003 | Sugiura |
| 6,561,986 B2 | 5/2003 | Baura |
| 6,564,077 B2 | 5/2003 | Mortara |
| 6,567,986 B2 | 5/2003 | Ward |
| 6,577,884 B1 | 6/2003 | Boas |
| 6,606,511 B1 | 8/2003 | Ali |
| 6,608,934 B2 | 8/2003 | Scheirer |
| 6,609,016 B1 | 8/2003 | Lynn |
| 6,654,623 B1 | 11/2003 | Kästle |
| 6,684,090 B2 | 1/2004 | Ali |
| 6,694,178 B1 | 2/2004 | Soula |
| 6,701,170 B2 | 3/2004 | Stetson |
| 6,702,752 B2 | 3/2004 | Dekker |
| 6,709,402 B2 | 3/2004 | Dekker |
| 6,748,252 B2 | 6/2004 | Lynn |
| 6,754,516 B2 | 6/2004 | Mannheimer |
| 6,760,608 B2 | 7/2004 | Lynn |
| 6,783,498 B2 | 8/2004 | Sackner |
| 6,801,798 B2 | 10/2004 | Geddes |
| 6,810,277 B2 | 10/2004 | Edgar |
| 6,811,538 B2 | 11/2004 | Westbrook |
| 6,816,741 B2 | 11/2004 | Diab |
| 6,819,950 B2 | 11/2004 | Mills |
| 6,839,581 B1 | 1/2005 | El-Solh |
| 6,839,582 B2 | 1/2005 | Heckel |
| 6,896,661 B2 | 5/2005 | Dekker |
| 6,905,470 B2 | 6/2005 | Lee |
| 6,909,912 B2 | 6/2005 | Melker |
| 6,918,878 B2 | 7/2005 | Brodnick |
| 6,925,324 B2 | 8/2005 | Shusterman |
| 6,930,608 B2 | 8/2005 | Grajales |
| 6,931,269 B2 | 8/2005 | Terry |
| 6,932,774 B2 | 8/2005 | Nakatani |
| 6,966,878 B2 | 11/2005 | Schoisswohl |
| 6,970,792 B1 | 11/2005 | Diab |
| 6,980,679 B2 | 12/2005 | Jeung |
| 6,985,763 B2 | 1/2006 | Boas |
| 6,990,426 B2 | 1/2006 | Yoon |
| 7,001,337 B2 | 2/2006 | Dekker |
| 7,020,507 B2 | 3/2006 | Scharf |
| 7,024,235 B2 | 4/2006 | Melker |
| 7,025,728 B2 | 4/2006 | Ito |
| 7,035,679 B2 | 4/2006 | Addison |
| 7,037,286 B1 | 5/2006 | Reinhardt |
| 7,043,293 B1 | 5/2006 | Baura |
| 7,044,918 B2 | 5/2006 | Diab |
| 7,052,469 B2 | 5/2006 | Minamiura |
| 7,054,453 B2 | 5/2006 | Causevic |
| 7,054,454 B2 | 5/2006 | Causevic |
| 7,070,566 B2 | 7/2006 | Medero |
| 7,079,880 B2 | 7/2006 | Stetson |
| 7,079,888 B2 | 7/2006 | Oung |
| 7,127,278 B2 | 10/2006 | Melker |
| 7,147,601 B2 | 12/2006 | Marks |
| 7,167,746 B2 | 1/2007 | Pederson |
| 7,171,251 B2 | 1/2007 | Sarussi |
| 7,171,269 B1 | 1/2007 | Addison |
| 7,173,525 B2 | 2/2007 | Albert |
| 7,177,682 B2 | 2/2007 | Lovett |
| 7,190,261 B2 | 3/2007 | Al-Ali |
| 7,203,267 B2 | 4/2007 | De Man |
| 7,215,986 B2 | 5/2007 | Diab |
| 7,215,991 B2 | 5/2007 | Besson |
| 7,218,966 B2 | 5/2007 | Haefner |
| 7,225,013 B2 | 5/2007 | Geva |
| 7,246,618 B2 | 7/2007 | Habashi |
| 7,254,425 B2 | 8/2007 | Lowery |
| 7,254,500 B2 | 8/2007 | Makeig |
| 7,283,870 B2 | 10/2007 | Kaiser |
| 7,289,835 B2 | 10/2007 | Mansfield |
| 7,336,982 B2 | 2/2008 | Yoo |
| 7,343,187 B2 | 3/2008 | Stetson |
| 7,344,497 B2 | 3/2008 | Kline |
| 7,355,512 B1 | 4/2008 | Al-Ali |
| 7,367,339 B2 | 5/2008 | Hickle |
| 7,367,949 B2 | 5/2008 | Korhonen |
| 7,381,185 B2 | 6/2008 | Zhirnov |
| 7,398,115 B2 | 7/2008 | Lynn |
| 7,403,806 B2 | 7/2008 | Norris |
| 7,407,486 B2 | 8/2008 | Huiku |
| 7,415,297 B2 | 8/2008 | Al-Ali |
| 7,421,296 B1 | 9/2008 | Benser |
| 7,438,683 B2 | 10/2008 | Al-Ali |
| 7,440,787 B2 | 10/2008 | Diab |
| 7,470,235 B2 | 12/2008 | Moriya |
| 7,485,095 B2 | 2/2009 | Shusterman |
| 7,496,393 B2 | 2/2009 | Diab |

(56) References Cited

U.S. PATENT DOCUMENTS

| | | |
|---|---|---|
| 7,499,835 B2 | 3/2009 | Weber |
| 7,515,949 B2 | 4/2009 | Norris |
| 7,519,488 B2 | 4/2009 | Fu |
| 7,523,011 B2 | 4/2009 | Akiyama |
| 7,561,912 B2 | 7/2009 | Schatz |
| 7,610,324 B2 | 10/2009 | Troyansky |
| 7,690,378 B1 | 4/2010 | Turcott |
| 7,792,571 B2 | 9/2010 | Sweeney |
| 7,801,591 B1 | 9/2010 | Shusterman |
| 7,869,980 B2 | 1/2011 | Casler |
| 7,894,868 B2 | 2/2011 | Al-Ali |
| 7,899,507 B2 | 3/2011 | Al-Ali |
| 7,975,472 B2 | 7/2011 | Halbei |
| 7,976,472 B2 | 7/2011 | Kiani |
| 7,988,637 B2 | 8/2011 | Diab |
| 8,019,400 B2 | 9/2011 | Diab |
| 8,046,040 B2 | 10/2011 | Al-Ali |
| 8,130,105 B2 | 3/2012 | Al-Ali |
| 8,140,143 B2 | 3/2012 | Picard |
| 8,203,438 B2 | 6/2012 | Kiani |
| 8,275,553 B2 | 9/2012 | Ochs |
| 8,364,223 B2 | 1/2013 | Al-Ali |
| 8,364,225 B2 | 1/2013 | Addison |
| 8,880,576 B2 | 11/2014 | Ochs |
| 2002/0117173 A1 | 8/2002 | Lynn |
| 2003/0028221 A1 | 2/2003 | Zhu |
| 2003/0033032 A1 | 2/2003 | Lind |
| 2003/0036685 A1 | 2/2003 | Goodman |
| 2003/0158466 A1 | 8/2003 | Lynn |
| 2003/0163054 A1 | 8/2003 | Dekker |
| 2003/0163057 A1 | 8/2003 | Flick |
| 2003/0212336 A1 | 11/2003 | Lee |
| 2003/0225337 A1 | 12/2003 | Scharf |
| 2004/0015091 A1 | 1/2004 | Greenwald |
| 2004/0260186 A1 | 12/2004 | Dekker |
| 2005/0004479 A1 | 1/2005 | Townsend |
| 2005/0022606 A1 | 2/2005 | Partin |
| 2005/0027205 A1 | 2/2005 | Tarassenko |
| 2005/0043616 A1 | 2/2005 | Chinchoy |
| 2005/0043763 A1 | 2/2005 | Marcovecchio |
| 2005/0049470 A1 | 3/2005 | Terry |
| 2005/0059869 A1 | 3/2005 | Scharf |
| 2005/0070774 A1 | 3/2005 | Addison |
| 2005/0109340 A1 | 5/2005 | Tehrani |
| 2005/0115561 A1* | 6/2005 | Stahmann ............ A61B 5/0031 128/200.24 |
| 2005/0209517 A1 | 9/2005 | Diab |
| 2005/0215915 A1 | 9/2005 | Noda |
| 2005/0222502 A1 | 10/2005 | Cooper |
| 2005/0222503 A1 | 10/2005 | Dunlop |
| 2005/0240091 A1 | 10/2005 | Lynn |
| 2005/0251056 A1 | 11/2005 | Gribkov |
| 2006/0074333 A1 | 4/2006 | Huiku |
| 2006/0122476 A1 | 6/2006 | Van Slyke |
| 2006/0155206 A1 | 7/2006 | Lynn |
| 2006/0192667 A1 | 8/2006 | Al-Ali |
| 2006/0209631 A1 | 9/2006 | Melese |
| 2006/0211930 A1 | 9/2006 | Scharf |
| 2006/0217603 A1 | 9/2006 | Nagai |
| 2006/0217614 A1 | 9/2006 | Takala |
| 2006/0229519 A1 | 10/2006 | Fujiwara |
| 2006/0241506 A1 | 10/2006 | Melker |
| 2006/0247506 A1 | 11/2006 | Balberg |
| 2006/0258921 A1 | 11/2006 | Addison |
| 2006/0265022 A1 | 11/2006 | John |
| 2006/0282001 A1 | 12/2006 | Noel |
| 2006/0293574 A1 | 12/2006 | Norris |
| 2007/0004977 A1 | 1/2007 | Norris |
| 2007/0010723 A1 | 1/2007 | Uutela |
| 2007/0021673 A1 | 1/2007 | Arbel |
| 2007/0032639 A1 | 2/2007 | Gottesman |
| 2007/0073120 A1 | 3/2007 | Li |
| 2007/0073124 A1 | 3/2007 | Li |
| 2007/0123756 A1 | 5/2007 | Kitajima |
| 2007/0129636 A1 | 6/2007 | Friedman |
| 2007/0129647 A1 | 6/2007 | Lynn |
| 2007/0142715 A1 | 6/2007 | Banet |
| 2007/0142719 A1 | 6/2007 | Kawasaki |
| 2007/0149883 A1 | 6/2007 | Yesha |
| 2007/0149890 A1 | 6/2007 | Li |
| 2007/0167694 A1 | 7/2007 | Causevic |
| 2007/0167851 A1 | 7/2007 | Vitali |
| 2007/0179369 A1 | 8/2007 | Baker |
| 2007/0213619 A1 | 9/2007 | Linder |
| 2007/0213621 A1 | 9/2007 | Reisfeld |
| 2007/0225581 A1 | 9/2007 | Diab |
| 2007/0239057 A1* | 10/2007 | Pu ..................... A61B 5/0816 600/529 |
| 2007/0255146 A1 | 11/2007 | Andrews |
| 2007/0282212 A1 | 12/2007 | Sierra |
| 2007/0293896 A1 | 12/2007 | Haefner |
| 2008/0045832 A1 | 2/2008 | McGrath |
| 2008/0060138 A1 | 3/2008 | Price |
| 2008/0066753 A1 | 3/2008 | Martin |
| 2008/0076992 A1 | 3/2008 | Hete |
| 2008/0077022 A1 | 3/2008 | Baker |
| 2008/0081325 A1 | 4/2008 | Mannheimer |
| 2008/0081961 A1 | 4/2008 | Westbrook |
| 2008/0082018 A1 | 4/2008 | Sackner |
| 2008/0091092 A1 | 4/2008 | Al-Ali |
| 2008/0167540 A1 | 7/2008 | Korhonen |
| 2008/0167541 A1 | 7/2008 | Takala |
| 2008/0171946 A1 | 7/2008 | Hansmann |
| 2008/0190430 A1 | 8/2008 | Melker |
| 2008/0200775 A1 | 8/2008 | Lynn |
| 2008/0202525 A1 | 8/2008 | Mitton |
| 2008/0214903 A1 | 9/2008 | Orbach |
| 2008/0243021 A1 | 10/2008 | Causevic |
| 2008/0316488 A1 | 12/2008 | Mao |
| 2009/0105601 A1 | 4/2009 | Kamata |
| 2009/0247837 A1 | 10/2009 | Ochs |
| 2009/0326349 A1 | 12/2009 | McGonigle |
| 2009/0326386 A1 | 12/2009 | Sethi |
| 2009/0326395 A1 | 12/2009 | Watson |
| 2009/0326402 A1 | 12/2009 | Addison |
| 2009/0326831 A1 | 12/2009 | McGonigle |
| 2010/0016680 A1 | 1/2010 | Addison |
| 2010/0113904 A1 | 5/2010 | Batchelder |
| 2010/0113908 A1 | 5/2010 | Vargas |
| 2010/0113909 A1 | 5/2010 | Batchelder |
| 2010/0286495 A1 | 11/2010 | McGonigle |
| 2010/0331715 A1 | 12/2010 | Addison |
| 2011/0004081 A1 | 1/2011 | Addison |
| 2011/0021892 A1 | 1/2011 | Addison |
| 2011/0028802 A1 | 2/2011 | Addison |
| 2011/0066007 A1 | 3/2011 | Banet |
| 2011/0066062 A1 | 3/2011 | Banet |
| 2011/0071406 A1 | 3/2011 | Addison |
| 2011/0077474 A1 | 3/2011 | Huiku |
| 2011/0275910 A1 | 11/2011 | Amos |
| 2012/0179061 A1 | 7/2012 | Ramanan |
| 2012/0253140 A1 | 10/2012 | Addison |
| 2012/0296219 A1 | 11/2012 | Chon |
| 2013/0006075 A1 | 1/2013 | Baker |
| 2013/0079606 A1 | 3/2013 | McGonigle |
| 2013/0245482 A1 | 9/2013 | McGonigle |
| 2013/0267791 A1 | 10/2013 | Halperin |
| 2013/0289413 A1 | 10/2013 | Ochs |

FOREIGN PATENT DOCUMENTS

| | | |
|---|---|---|
| EP | 1507474 | 2/2005 |
| JP | 09-084776 | 3/1997 |
| WO | WO 92/015955 | 9/1992 |
| WO | WO 00/021438 | 4/2000 |
| WO | WO 01/025802 | 4/2001 |
| WO | WO 01/062152 | 8/2001 |
| WO | WO 01/076471 | 10/2001 |
| WO | WO 01/082099 | 11/2001 |
| WO | WO 03/000125 | 1/2003 |
| WO | WO 03/055395 | 7/2003 |
| WO | WO 03/084396 | 10/2003 |
| WO | WO 04/075746 | 9/2004 |
| WO | WO 04/105601 | 12/2004 |

(56) References Cited

FOREIGN PATENT DOCUMENTS

| WO | WO 05/064314 | 7/2005 |
|---|---|---|
| WO | WO 05/096170 | 10/2005 |
| WO | WO 06/085120 | 8/2006 |
| WO | WO 08/043864 | 4/2008 |
| WO | WO 08/134813 | 11/2008 |
| WO | WO 10/001248 | 1/2010 |
| WO | WO 10/030238 | 3/2010 |

OTHER PUBLICATIONS

Gil et al., Study of the relationship between Pulse Photopletismography amplitude decrease events and sleep apneas in children, Proceedings of the 28th IEEE EMBS Annual International Conference New York City, USA, Aug. 30-Sep. 3, 2006.*

Gil et al., Discrimination of Sleep-Apnea-Related Decreases in the Amplitude Fluctuations of PPG Signal in Children by HRV Analysis, IEEE Transactions on Biomedical Engineering, vol. 56, No. 4, Apr. 2009.*

Elgendi M, On the Analysis of Fingertip Photoplethysmogram Signals, Current Cardiology Reviews, 2012, 8, 14-25.*

U.S. Appl. No. 14/519,045, filed Oct. 20, 2014, Covidien LP.

U.S. Appl. No. 14/523,080, filed Oct. 24, 2014, Covidien LP.

Aapo Hyvarinen and Erkki Oja, "Independent Component Analysis: Algorithms and Applications," Neural Networks, 13(4-5), pp. 411-430, 2000.

Addison, Paul S., "The Illustrated Wavelet Transform Handbook," Taylor & Francis Group, 2002.

Addison, Paul S., "The Little Wave with the Big Future," Physics World, Mar. 2004, pp. 35-39.

Clifton, David, et al. "Measurement of Respiratory Rate from the Photoplethysmogram in Chest Clinic Patients," Journal of Clinical Monitoring and Computing, 2006.

Legarreta, I. Romero, et al., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2005, pp. 1-24.

Leonard, Paul A., et al., "A Fully Automated Algorithm for the Determination of Respiratory Rate from the Photoplethysmogram," Journal of Clinical Monitoring and Computing, vol. 20, No. 1, pp. 33-36, 2006.

Leonard, Paul A., "An Automated Algorithm for Determining Respiratory Rate by Photoplethysmogram in Children," Acta Paediatricia, 2006; 95: pp. 1124-1128.

Lindberg, L.G., Ughall, H., Oberg, P.A., "Monitoring of Respiratory and Heart Rates Using a Fibre-Optic Sensor," Medical & Biological Engineering & Computing, Sep. 1992, pp.533-537.

Rapaport and Cousin, "New Phase-Lock Tracking Instrument for Foetal Breathing Monitoring," Med. & Biol. Eng. & Comput., Jan. 1982, vol. 20, pp. 1-6.

Stagg and Gennser, "Electronic Analysis of Foetal Breathing Movements: A practical Application of Phase-Locked-Loop Principles," Journal of Med. Eng. and Tech., Sep. 5, 1978, vol. 2, No. 5, pp. 246-249.

The FastICA Algorithm for Independent Component Analysis and Projection Pursuit, Dec. 21, 2010.

Yamada, Michio, "Wavelet Analysis and Its Application," Journal of the Institute of Electronics, Information and Communication Engineers, vol. 76. No. 5, May 1993, pp. 518-528.

International Search Report for Application No. PCT/US2012/056636, dated Jan. 23, 2013.

International Search Report for Application No. PCT/GB2010/000837, dated Sep. 10, 2010.

International Search Report for Application No. PCT/US2014/062230, dated Jan. 27, 2015.

* cited by examiner

SYSTEMS AND METHODS FOR DETECTING HELD BREATH EVENTS

CROSS-REFERENCE TO RELATED APPLICATION

The present disclosure claims priority to U.S. Provisional Application No. 61/896,538, filed on Oct. 28, 2013, which is hereby incorporated by reference herein in its entirety.

FIELD OF THE DISCLOSURE

The present disclosure relates to physiological signal processing, and more particularly relates to identifying held breath events from a physiological signal.

SUMMARY

The present disclosure provides a computer-implemented method comprising: receiving a photoplethysmograph (PPG) signal; generating, using processing circuitry, one or more respiration morphology signals based on the PPG signal; calculating, using the processing circuitry, a threshold value for each of the one or more respiration morphology signals; comparing, using the processing circuitry, data indicative of each morphology signal to a respective one of the threshold values; and identifying, using the processing circuitry, a held breath event based at least on the comparing.

The present disclosure provides a system comprising: an input for receiving a photoplethysmograph (PPG) signal; and processing circuitry configured for: generating one or more respiration morphology signals based on the PPG signal, calculating a threshold value for each of the one or more respiration morphology signals, comparing data indicative of each morphology signal to a respective one of the threshold values, and identifying a held breath event based at least on the comparing.

The present disclosure provides a non-transitory computer readable medium comprising instructions stored therein for performing the method comprising: receiving a photoplethysmograph (PPG) signal; generating one or more respiration morphology signals based on the PPG signal; calculating a threshold value for each of the one or more respiration morphology signals; comparing data indicative of each morphology signal to a respective one of the threshold values; and identifying a held breath event based at least on the comparing.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
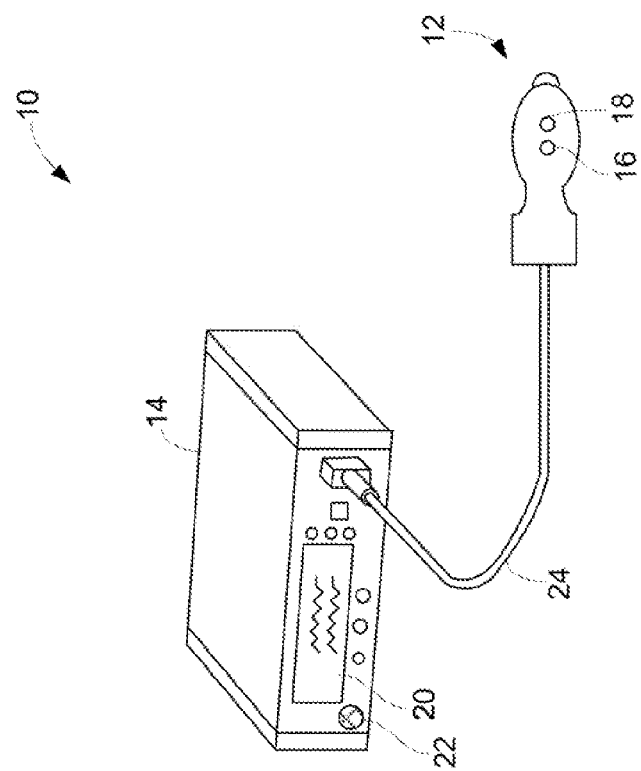
FIG. 1 shows an illustrative patient monitoring system in accordance with some embodiments of the present disclosure.

A physiological signal such as a photoplethysmograph (PPG) signal may be indicative of pulsatile blood flow. Pulsatile blood flow may be dependent on a number of physiological functions such as cardiovascular function and respiration. For example, the PPG signal may exhibit a periodic component that generally corresponds to the heart beat of a patient. This pulsatile component of the PPG signal may be used to determine physiological parameters such as heart rate.

Respiration may also impact the pulsatile blood flow that is indicated by the PPG signal. It may thus be possible to calculate respiration information such as respiration rate from the PPG signal. However, in some instances a patient's actions such as talking or holding of breath may temporarily disrupt respiration, and thus the respiratory modulations to the PPG signal. It may therefore be desirable to identify patient actions such as held breath events when determining respiration information such as respiration rate.

As with other respiration events, a held breath event may result in changes to the pulsatile blood flow that is indicated by the PPG signal. It may be desirable to identify held breath events based on these changes to the blood flow indicated by the PPG signal.

For purposes of clarity, the present disclosure is written in the context of the physiological signal being a PPG signal generated by a pulse oximetry system. It will be understood that any other suitable physiological signal or any other suitable system may be used in accordance with the teachings of the present disclosure.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations that are not typically understood to be optimal for pulse oximetry serve as suitable sensor locations for the monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t)=I_0(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_0$=intensity of light transmitted;
S=oxygen saturation;
$\beta_o, \beta_r$=empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield $$\log I=\log I_o-(s\beta_o+(1-s)\beta_r)l. \quad (2)$$

2. Eq. 2 is then differentiated with respect to time to yield $$\frac{d\log I}{dt} = -(s\beta_o + (1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with $$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})}. \quad (4)$$

4. Solving for S yields $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}. \quad (5)$$

5. Note that, in discrete time, the following approximation can be made:

$$\frac{d\log I(\lambda, t)}{dt} \simeq \log I(\lambda, t_2) - \log I(\lambda, t_1). \quad (6)$$

6. Rewriting Eq. 6 by observing that log A−log B=log(A/B) yields $$\frac{d\log I(\lambda, t)}{dt} \simeq \log\left(\frac{I(t_2, \lambda)}{I(t_1, \lambda)}\right). \quad (7)$$

7. Thus, Eq. 4 can be expressed as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \quad (8)$$

where R represents the "ratio of ratios."

8. Solving Eq. 4 for S using the relationship of Eq. 5 yields $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}. \quad (9)$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{dI/dt}{I}, \quad (10)$$

Eq. 8 becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (11)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R,$$

which defines a cluster of points whose slope of y versus x will give R when $$x=[I(t_2,\lambda_{IR})-I(t_1,\lambda_{IR})]I(t_1,\lambda_R), \quad (12)$$

and $$y=[I(t_2,\lambda_R)-I(t_1,\lambda_R)]I(t_1,\lambda_{IR}). \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

FIG. 1 is a perspective view of an embodiment of a patient monitoring system 10. System 10 may include sensor unit 12 and monitor 14. In some embodiments, sensor unit 12 may be part of an oximeter. Sensor unit 12 may include an emitter 16 for emitting light at one or more wavelengths into a patient's tissue. A detector 18 may also be provided in sensor unit 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a patient's forehead, while a second sensor unit may be positioned at a patient's fingertip.

Sensor units may each detect any signal that carries information about a patient's physiological state, such as an electrocardiograph signal, arterial line measurements, or the pulsatile force exerted on the walls of an artery using, for example, oscillometric methods with a piezoelectric transducer. According to some embodiments, system 10 may include two or more sensors forming a sensor array in lieu of either or both of the sensor units. Each of the sensors of a sensor array may be a complementary metal oxide semiconductor (CMOS) sensor. Alternatively, each sensor of an array may be charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In some embodiments, emitter 16 and detector 18 may be arranged so that light from emitter 16 penetrates the tissue and is reflected by the tissue into detector 18, such as in a sensor designed to obtain pulse oximetry data from a patient's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood oxygen saturation (e.g., $SpO_2$), and respiration information) based at least in part on data relating to light emission and detection received from one or more sensor units such as sensor unit 12 and an additional sensor (not shown). In some embodiments, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may allow communication between monitor 14 and sensor unit 12.

As is described herein, monitor 14 may generate a PPG signal based on the signal received from sensor unit 12. The PPG signal may consist of data points that represent a pulsatile waveform. The pulsatile waveform may be modulated based on the respiration of a patient. Respiratory modulations may include baseline modulations, amplitude modulations, frequency modulations, respiratory sinus arrhythmia, any other suitable modulations, or any combination thereof. Respiratory modulations may exhibit different phases, amplitudes, or both, within a PPG signal and may contribute to complex behavior (e.g., changes) of the PPG signal. For example, the amplitude of the pulsatile waveform may be modulated based on respiration (amplitude modulation), the frequency of the pulsatile waveform may be modulated based on respiration (frequency modulation), and a signal baseline for the pulsatile waveform may be modulated based on respiration (baseline modulation). Monitor 14 may analyze the PPG signal (e.g., by generating respiration morphology signals from the PPG signal, generating a combined autocorrelation sequence based on the respiration morphology signals, and calculating respiration information from the combined autocorrelation sequence) to determine respiration information based on one or more of these modulations of the PPG signal.

As is described herein, respiration information may be determined from the PPG signal by monitor 14. However, it will be understood that the PPG signal could be transmitted to any suitable device for the determination of respiration information, such as a local computer, a remote computer, a nurse station, mobile devices, tablet computers, or any other device capable of sending and receiving data and performing processing operations. Information may be transmitted from monitor 14 in any suitable manner, including wireless (e.g., WiFi, Bluetooth, etc.), wired (e.g., USB, Ethernet, etc.), or application-specific connections. The receiving device may determine respiration information as described herein.

Figure 2:
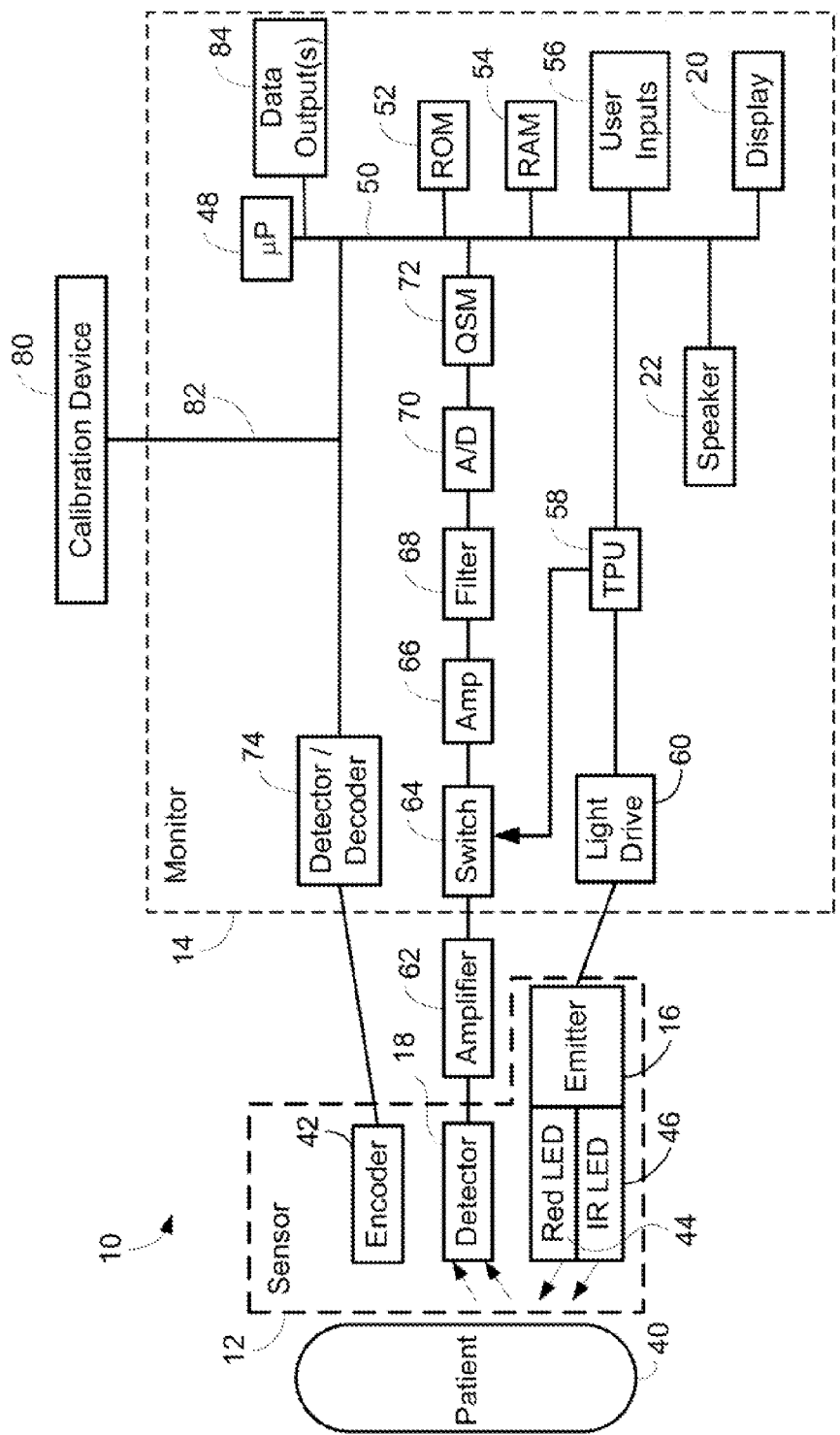
FIG. 2 is a block diagram of the illustrative patient monitoring system of FIG. 1 coupled to a patient in accordance with some embodiments of the present disclosure.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In some embodiments, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor may emit only a Red light while a second sensor may emit only an IR light. In a further example, the wavelengths of light used may be selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In some embodiments, encoder 42 may contain information about sensor unit 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which measurements may be determined based at least in part on the signal or signals received at sensor unit 12. For example, some pulse oximetry sensors rely on equations to relate an area under a portion of a PPG signal corresponding to a physiological pulse to determine blood pressure. These equations may contain coefficients that depend upon a patient's physiological characteristics as stored in encoder 42.

Encoder 42 may, for instance, be a coded resistor that stores values corresponding to the type of sensor unit 12 or the type of each sensor in the sensor array, the wavelengths of light emitted by emitter 16 on each sensor of the sensor array, and/or the patient's characteristics and treatment information. In some embodiments, encoder 42 may include a memory on which one or more of the following information may be stored for communication to monitor 14; the type of the sensor unit 12; the wavelengths of light emitted by emitter 16; the particular wavelength each sensor in the sensor array is monitoring; a signal threshold for each sensor in the sensor array; any other suitable information; physiological characteristics (e.g., gender, age, weight); or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, data output 84, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment" or "processing circuitry."

In some embodiments, microprocessor 48 may determine the patient's physiological parameters, such as $SpO_2$, pulse rate, and/or respiration information, using various algorithms and/or look-up tables based on the value of the received signals and/or data corresponding to the light received by detector 18. As is described herein, microprocessor 48 may generate respiration morphology signals and determine respiration information from a PPG signal.

Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable microprocessor 48 to determine the thresholds based at least in part on algorithms or look-up tables stored in ROM 52. In some embodiments, user inputs 56 may be used to enter information, select one or more options, provide a response, input settings, any other suitable inputting function, or any combination thereof. User inputs 56 may be used to enter information about the patient, such as age, weight, height, diagnosis, medications, treatments, and so forth. In some embodiments, display 20 may exhibit a list of values, which may generally apply to the patient, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Data output 84 may provide for communications with other devices utilizing any suitable transmission medium, including wireless (e.g., WiFi, Bluetooth, etc.), wired (e.g., USB, Ethernet, etc.), or application-specific connections. Data output 84 may receive messages to be transmitted from microprocessor 48 via bus 50. Exemplary messages to be sent in an embodiment described herein may include samples of the PPG signal to be transmitted to an external device for determining respiration information.

The optical signal attenuated by the tissue of patient 40 can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. Also, because blood is a fluid, it responds differently than the surrounding tissue to inertial effects, which may result in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals, control the amount of noise present in the signal, or otherwise identify noise components in order to prevent them from affecting measurements of physiological parameters derived from the sensor signals.

Figure 3:
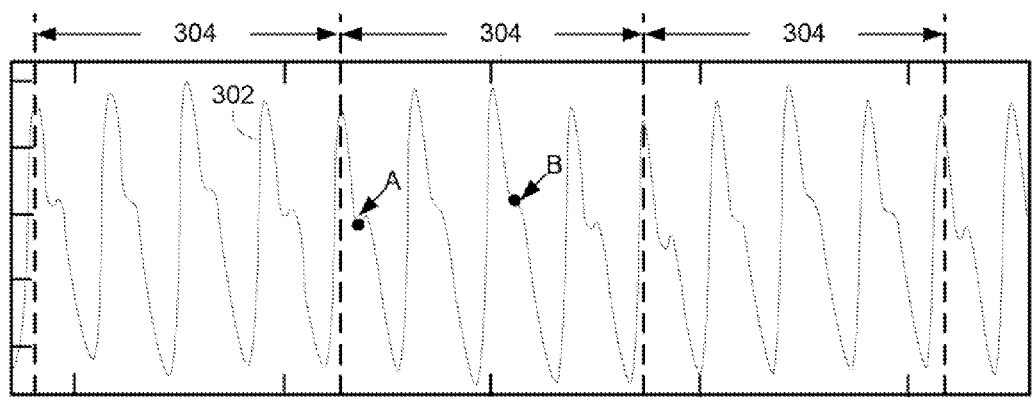
FIG. 3 shows an illustrative PPG signal that is modulated by respiration in accordance with some embodiments of the present disclosure.

FIG. 3 shows an illustrative PPG signal 302 that is modulated by respiration in accordance with some embodiments of the present disclosure. PPG signal 302 may be a periodic signal that is indicative of changes in pulsatile blood flow. Each cycle of PPG signal 302 may generally correspond to a pulse, such that a heart rate may be determined based on PPG signal 302. Each respiratory cycle 304 may correspond to a breath. The period of a respiratory cycle may typically be longer than the period of a pulsatile cycle, such that any changes in the pulsatile blood flow due to respiration occur over a number of pulsatile cycles. The volume of the pulsatile blood flow may also vary in a periodic manner based on respiration, resulting in modulations to the pulsatile blood flow such as amplitude modulation, frequency modulation, and baseline modulation. This modulation of PPG signal 302 due to respiration may result in changes to the morphology of PPG signal 302.

Figure 4:
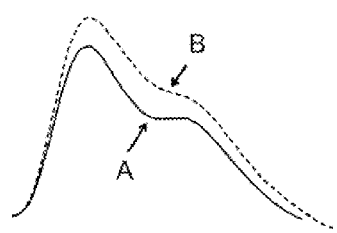
FIG. 4 shows a comparison of portions of the illustrative PPG signal of FIG. 3 in accordance with some embodiments of the present disclosure.

FIG. 4 shows a comparison of portions of the illustrative PPG signal 302 of FIG. 3 in accordance with some embodiments of the present disclosure. The signal portions compared in FIG. 4 may demonstrate differing morphology due to respiration modulation based on the relative location of the signal portions within a respiratory cycle 304. For example, a first pulse associated with the respiratory cycle may have a relatively low amplitude (indicative of amplitude and baseline modulation) as well as an obvious distinct dichrotic notch as indicated by point A. A second pulse may have a relatively high amplitude (indicative of amplitude and baseline modulation) as well as a dichrotic notch that has been washed out as depicted by point B. Frequency modulation may be evident based on the relative period of the first pulse and second pulse. Referring again to FIG. 3, by the end of the respiratory cycle 304 the pulse features may again be similar to the morphology of A. Although the impact of respiration modulation on the morphology of a particular PPG signal 302 has been described herein, it will be understood that respiration may have varied effects on the morphology of a PPG signal other than those depicted in FIGS. 3 and 4.

Figure 5:
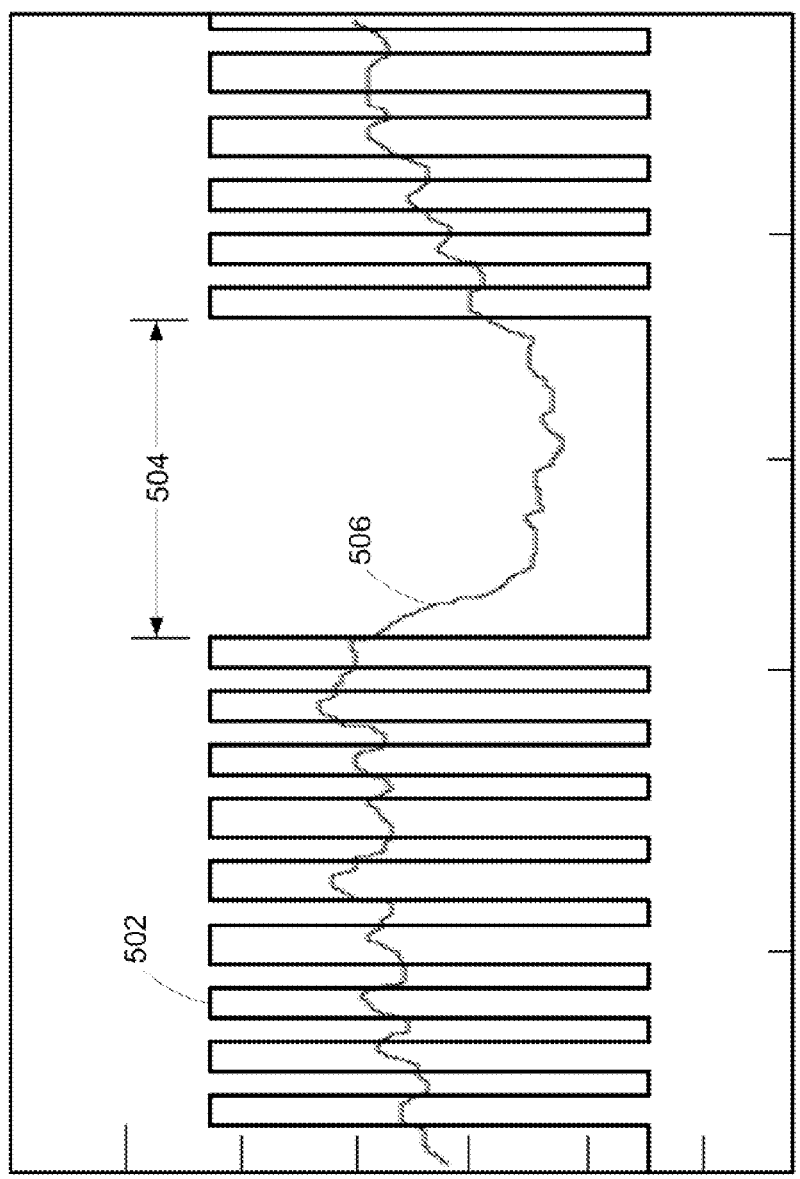
FIG. 5 shows an exemplary held breath event in accordance with some embodiments of the present disclosure.

When a patient stops breathing either voluntarily or involuntarily, this may be referred to as a held breath event. FIG. 5 shows an example of a held breath event in accordance with some embodiments of the present disclosure. Square wave signal 502 represents actual breathing over time, with each square wave cycle corresponding to a breath. A held breath portion 504 of the square wave respiration signal 502 demonstrates a portion of respiration signal 502 during which the patient is having a held breath event. In some embodiments, a respiration signal, such as signal 502, may be generated from a physiological signal such as a PPG signal (e.g., based on modulations to the PPG signal corresponding to respiration), a sound signal (e.g., based on sounds corresponding to an inhalation or exhalation), an airflow signal (e.g., to directly detect inhalation or exhalation), an acceleration signal (e.g., attached to a patient's chest to detect breathing), any other suitable physiological signal, or any combination thereof. In an embodiment, respiration information signal 506 may be an exemplary representation of the signal energy of a respiration signal, which may correspond to the detected patient respiration. As is depicted in FIG. 5, respiration information signal 506 may decrease in strength significantly during a held breath event such as held breath event 504. As is described herein, a detector for held breath events may utilize this decrease in signal amplitude to identify held breath events based on a physiological signal.

Figure 6:
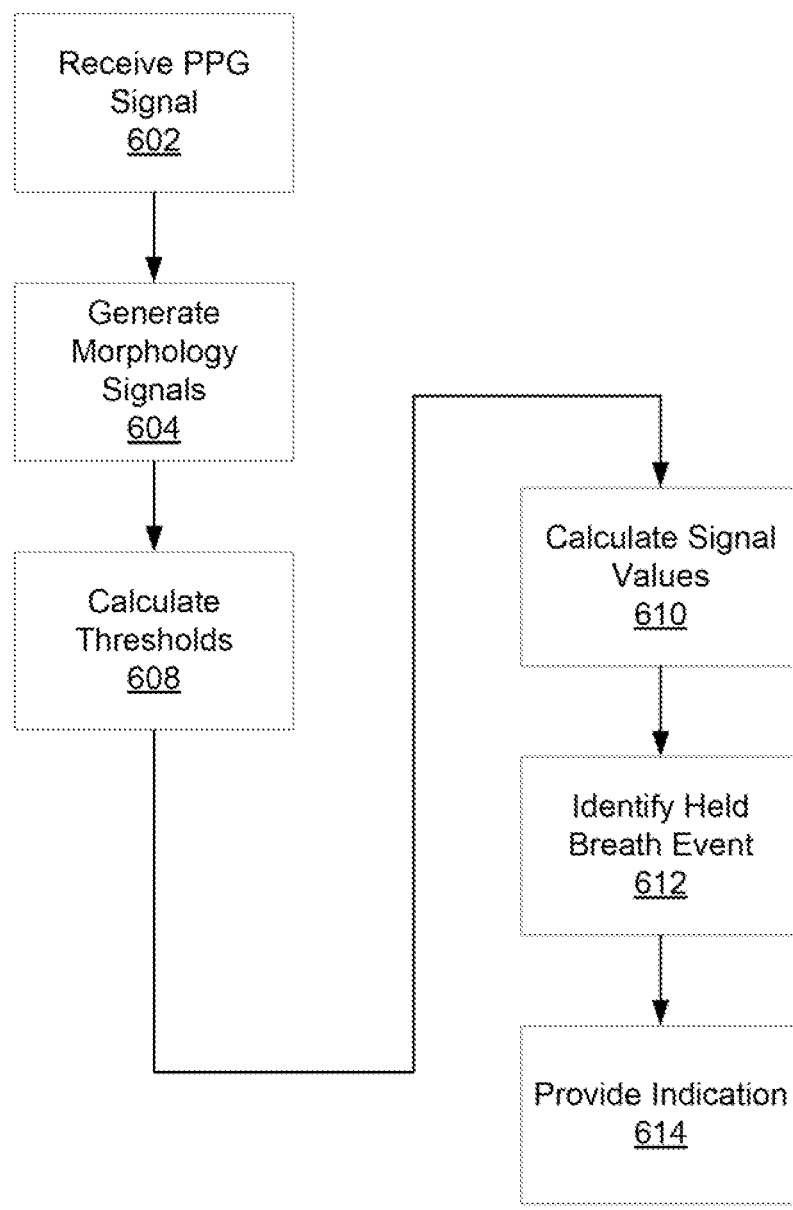
FIG. 6 shows illustrative steps for identifying a held breath event in accordance with some embodiments of the present disclosure.

FIG. 6 shows illustrative steps for identifying a held breath event from a PPG signal in accordance with some embodiments of the present disclosure. Although exemplary steps are described herein, it will be understood that steps may be omitted and that any suitable additional steps may be added for determining respiration information. Although the steps described herein may be performed by any suitable device, in an exemplary embodiment, the steps may be performed by monitoring system 10. At step 602, monitoring system 10 may receive a PPG signal as described herein. Although the PPG signal may be processed in any suitable manner, in an embodiment, the PPG signal may be analyzed each 5 seconds, and for each 5 second analysis window, the most recent 45 seconds of the PPG signal may be analyzed.

At step 604, monitoring system 10 may generate one or more respiration morphology signals from the PPG signal. Although respiration morphology signals may be used to calculate respiration information such as respiration rate, as described herein the respiration morphology signals may also be used to identify held breath events.

Any suitable number of respiration morphology signals may be generated from a PPG signal. In an exemplary embodiment, a down signal, a delta of second derivative (DSD) signal, a kurtosis signal, a b/a ratio signal, any other suitable morphology signal (such as those discussed below), or any combination thereof may be generated. Although a respiration morphology signal may be generated in any suitable manner, in an exemplary embodiment, each respiration morphology signal may be generated based on calculating a series of morphology metrics based on a PPG signal. One or more morphology metrics maybe calculated for each portion of the PPG signal (e.g., for each fiducial defined portion), a series of morphology metrics may be calculated over time, and the series of morphology metrics may be processed to generate one or more respiration morphology signals.

Figure 7:
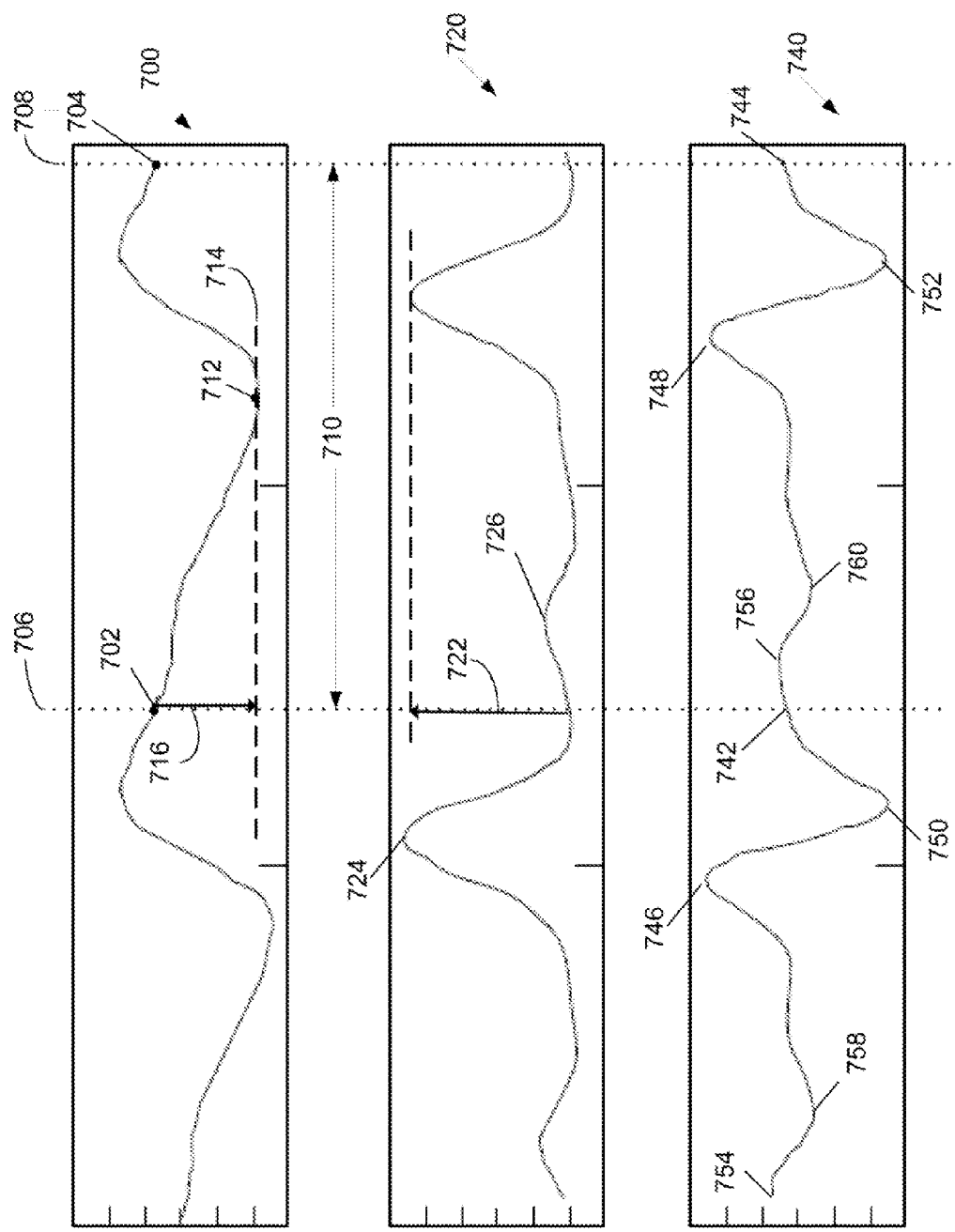
FIG. 7 shows an illustrative PPG signal, a first derivative of the PPG signal, and a second derivative of the PPG signal in accordance with some embodiments of the present disclosure.

FIG. 7 depicts signals used for calculating morphology metrics from a received PPG signal. The abscissa of each plot of FIG. 7 may be represent time and the ordinate of each plot may represent magnitude. PPG signal 700 may be a received PPG signal, first derivative signal 720 may be a signal representing the first derivative of the PPG signal 700, and second derivative signal 740 may be a signal representing the second derivative of the PPG signal 700. Although particular morphology metric determinations are set forth below, each of the morphology metric calculations may be modified in any suitable manner. Any of a plurality of morphology metrics may be utilized in combination to determine respiration information.

Exemplary fiducial points 702 and 704 are depicted for PPG signal 700, and fiducial lines 706 and 708 demonstrate the location of fiducial points 702 and 704 relative to first derivative signal 720 and second derivative signal 740. Fiducial points 702 and 704 may define a fiducial-defined portion 710 of PPG signal 700. The fiducial points 702 and 704 may define starting ending points for determining morphology metrics as described herein, and the fiducial-defined portion 710 may be define a relevant portion of data for determining morphology metrics as described herein. It will be understood that other starting points, ending points, and relative portions of data may be utilized to determine morphology metrics.

An exemplary morphology metric may be a down metric. The down metric is the difference between a first (e.g., fiducial) sample of a fiducial-defined portion (e.g., fiducial defined portion 710) of the PPG signal (e.g., PPG signal 700) and a minimum sample (e.g., minimum sample 712) of the fiducial-defined portion of the PPG signal. A down metric may also be calculated based on other points of a fiducial-defined portion. The down metric is indicative of physiological characteristics which are related to respiration, e.g., amplitude and baseline modulations of the PPG signal. In an exemplary embodiment fiducial point 702 defines the first location for calculation of a down metric for fiducial-defined portion 710. In the exemplary embodiment the minimum sample of fiducial-defined portion 710 is minimum point 712, and is indicated by horizontal line 714. The down metric may be calculated by subtracting the value of minimum point 712 from the value of fiducial point 702, and is depicted as down metric 716.

Another exemplary morphology metric may be a kurtosis metric for a fiducial-defined portion. Kurtosis measures the peakedness of the first derivative 720 of the PPG signal. The peakedness is sensitive to both amplitude and period (frequency) changes, and may be utilized as an input to determine respiration information, such as respiration rate. Kurtosis may be calculated based on the following formulae:

$$D = \frac{1}{n}\sum_{i=1}^{n} (x'_i - \overline{x'})^2$$

$$\text{Kurtosis} = \frac{1}{nD^2}\sum_{i=1}^{n} (x'_i - \overline{x'})^4$$

where:
$x'_i$=ith sample of $1^{st}$ derivative;
$\overline{x'}$=mean of 1st derivative of fiducial-defined portion;
n=set of all samples in the fiducial-defined portion Another exemplary morphology metric may be a delta of the second derivative (DSD) between consecutive fiducial-defined portions, e.g., at consecutive fiducial points. Measurement points 742 and 744 for a DSD calculation are depicted at fiducial points 702 and 704 as indicated by fiducial lines 706 and 708. The second derivative is indicative of the curvature of a signal. Changes in the curvature of the PPG signal are indicative of changes in internal pressure that occur during respiration, particularly changes near the peak of a pulse. By providing a metric of changes in curvature of the PPG signal, the DSD morphology metric may be utilized as an input to determine respiration information, such as respiration rate. The DSD metric may be calculated for each fiducial-defined portion by subtracting the second derivative of the next fiducial point from the second derivative of the current fiducial point.

Another exemplary morphology metric may be an up metric measuring the up stroke of the first derivative signal 720 of the PPG signal. The up stroke may be based on an initial starting sample (fiducial point) and a maximum sample for the fiducial-defined portion and is depicted as up metric 722 for a fiducial point corresponding to fiducial line 706. The up metric may be indicative of amplitude and baseline modulation of the PPG signal, which may be related to respiration information as described herein. Although an up metric is described herein with respect to the first derivate signal 720, it will be understood that an up metric may also be calculated for the PPG signal 700 and second derivative signal 740.

Another exemplary morphology metric may be a skew metric measuring the skewness of the original PPG signal 700 or first derivative 720. The skew metric is indicative of how tilted a signal is, and increases as the PPG signal is compressed (indicating frequency changes in respiration) or the amplitude is increased. The skewness metric is indicative of amplitude and frequency modulation of the PPG signal, which may be related to respiration information as described herein. Skewness may be calculated as follows:

$$g1 = \frac{m_3}{m_2^{3/2}} = \frac{\frac{1}{n}\sum_{i=1}^{n}(x_i - \bar{x})^3}{\left(\frac{1}{n}\sum_{i=1}^{n}(x_i - \bar{x})^2\right)^{3/2}}$$

where:
$x_i$=ith sample;
$\bar{x}$=mean of the samples of the fiducial-defined portion;
$m_3$=third moment;
$m_2$=second moment; and
n=total number of samples.

Another exemplary morphology metric may be a b/a ratio metric (i.e., b/a), which is based on the ratio between the a-peak and b-peak of the second derivative signal 740. PPG signal 700, first derivative signal 720, and second derivative signal 700 may include a number of peaks (e.g., four peaks corresponding to maxima and minima) which may be described as the a-peak, b-peak, c-peak, and d-peak, with the a-peak and c-peak generally corresponding to local maxima within a fiducial defined portion and the b-peak and d-peak generally corresponding to local minima within a fiducial defined portion. For example, the second derivative of the PPG signal may include four peaks: the a-peak, b-peak, c-peak, and d-peak. Each peak may be indicative of a respective systolic wave, i.e., the a-wave, b-wave, c-wave, and d-wave. On the depicted portion of the second derivative of the PPG signal 740, the a-peaks are indicated by points 746 and 748, the b-peaks by points 750 and 752, the c-peaks by points 754 and 756, and the d-peaks by points 758 and 760. The b/a ratio measures the ratio of the b-peak (e.g., 750 or 752) and the a-peak (e.g., 746 or 748). The b/a ratio metric may be indicative of the curvature of the PPG signal, which demonstrates frequency modulation based on respiration information such as respiration rate. The b/a ratio may also be calculated based on the a-peak and b-peak in higher order signals such as PPG signal and first derivative PPG signal 720.

Another exemplary morphology metric may be a c/a ratio (i.e., c/a), which is calculated from the a-peak and c-peak of a signal. For example, first derivate PPG signal 720 may have a c-peak 726 which corresponds to the maximum slope near the dichrotic notch of PPG signal 700, and an a-peak 724 which corresponds to the maximum slope of the PPG signal 700. The c/a ratio of the first derivative is indicative of frequency modulation of the PPG signal, which is related to respiration information such as respiration rate as described herein. A c/a ratio may be calculated in a similar manner for PPG signal 700 and second derivative signal 740.

Another exemplary morphology metric may be a i_b metric measuring the time between two consecutive local minimum (b) locations 750 and 752 in the second derivative 740. The i_b metric is indicative of frequency modulation of the PPG signal, which is related to respiration information such as respiration rate as described herein. The i_b metric may also be calculated for PPG signal 700 or first derivative signal 720.

Another exemplary morphology metric may be a peak amplitude metric measuring the amplitude of the peak of the original PPG signal 700 or of the higher order derivatives 720 and 740. The peak amplitude metric is indicative of amplitude modulation of the PPG signal, which is related to respiration information such as respiration rate as described herein.

Another exemplary morphology metric may be a center of gravity metric measuring the center of gravity of a fiducial-defined portion from the PPG signal 700 in either or both of the x and y coordinates. The center of gravity is calculated as follows:

Center of gravity$(x) = \Sigma(x_i * y_i)/\Sigma y_i$

Center of gravity$(y) = \Sigma(x_i * y_i)/\Sigma x_i$

The center of gravity metric of the x coordinate for a fiducial-defined portion is indicative of frequency modulation of the PPG signal, which is related to respiration information such as respiration rate as described herein. The center of gravity metric of the y coordinate for a fiducial-defined portion is indicative of amplitude modulation of the PPG signal, which is related to respiration information such as respiration rate as described herein.

Another exemplary morphology metric is an area metric measuring the total area under the curve for a fiducial-defined portion of the PPG signal 700. The area metric is indicative of frequency and amplitude modulation of the PPG signal, which is related to respiration information such as respiration rate as described herein.

Another morphology metric is the PPG amplitude metric. This metric represents the amplitude of the patient's PPG signal. In some embodiments, the PPG amplitude metric is normalized to the baseline (i.e., DC component) of the underlying PPG signal.

Another morphology metric is the PPG amplitude modulation metric. This metric represents the modulation of amplitude over time on a patient's PPG signal.

Another morphology metric is the frequency modulation metric. This metric represents the modulation of periods between fiducial points on a physiological signal, such as a PPG signal.

Although a number of morphology metrics have been described herein, it will be understood that other morphology metrics may be calculated from PPG signal 700, first derivative signal 720, second derivative signal 740, and any other order of the PPG signal. It will also be understood that any of the morphology metrics described above may be modified to capture aspects of respiration information or other physiological information that may be determined from a PPG signal.

Referring again to FIG. 6, at step 604 a series of morphology metric values may be calculated for each morphology metric (e.g., down, kurtosis, DSD, b/a ratio, PPG amplitude, PPG amplitude modulation, and frequency modulation). In some embodiments, each series of morphology metric values may be further processed in any suitable manner to generate the respiration morphology signals. Although any suitable processing operations may be performed for each series of morphology metric values, in an exemplary embodiment, each series of morphology metric values may be filtered (e.g., based on frequencies associated with respiration) and interpolated to generate the respiration morphology signals.

At step 608, monitor 10 may calculate thresholds for use in identifying held breath events. As will be described herein, steps 608-612 describe a procedure for calculating thresholds for one or more of the respiration morphology signals and the pulsatile metric signals (at step 608), calculating average values associated with each of the one or more of the respiration morphology signals (at step 610), and identifying a held breath event based on a comparison of the thresholds and the average values (at step 612).

Although thresholds may be calculated for the one or more respiration morphology signals in any suitable manner, in some embodiments, the threshold may be based on a history of the mean absolute deviation for each of the one or more signals. For each of the one or more morphology signals, the mean absolute deviation may be calculated for any suitable portion of signal. For example, the mean absolute deviation may be calculated once for the respiration morphology signal for each 5 second window of received PPG data. The mean absolute deviation may be combined with a suitable number of previous windows, such as the 9 most previous windows (e.g., the mean absolute deviation may be calculated for each morphology signal for each 5 second window, and the 10 windows may be combined) to generate a combined value. This combination may be, for example, a weighted average of the 10 mean absolute deviation values. Weights may be fixed or determined based on any suitable criteria, such as signal quality. The combined value may be used as the threshold value. In some embodiments, the threshold value may be calculated from the combined value by multiplying the combined value by any suitable constant (e.g., determined based on empirical data).

At step 610, monitor 10 may calculate average values for each of the one or more respiration morphology signals to compare against respective thresholds that were calculated as discussed above, for example. As described herein, in an embodiment, average values may be calculated for the down, kurtosis, DSD, and b/a, the frequency modulation, pulse amplitude, and pulse amplitude modulation morphology signals.

Although it will be understood that the average values may be calculated in any suitable manner, in an embodiment, the average values may be calculated based on the average signal energy for the most recent 20 seconds of each of the respiration morphology signals. The average for each morphology signal may be calculated using weights, which may be fixed or determined based on any suitable criteria, such as signal quality.

Figure 8:
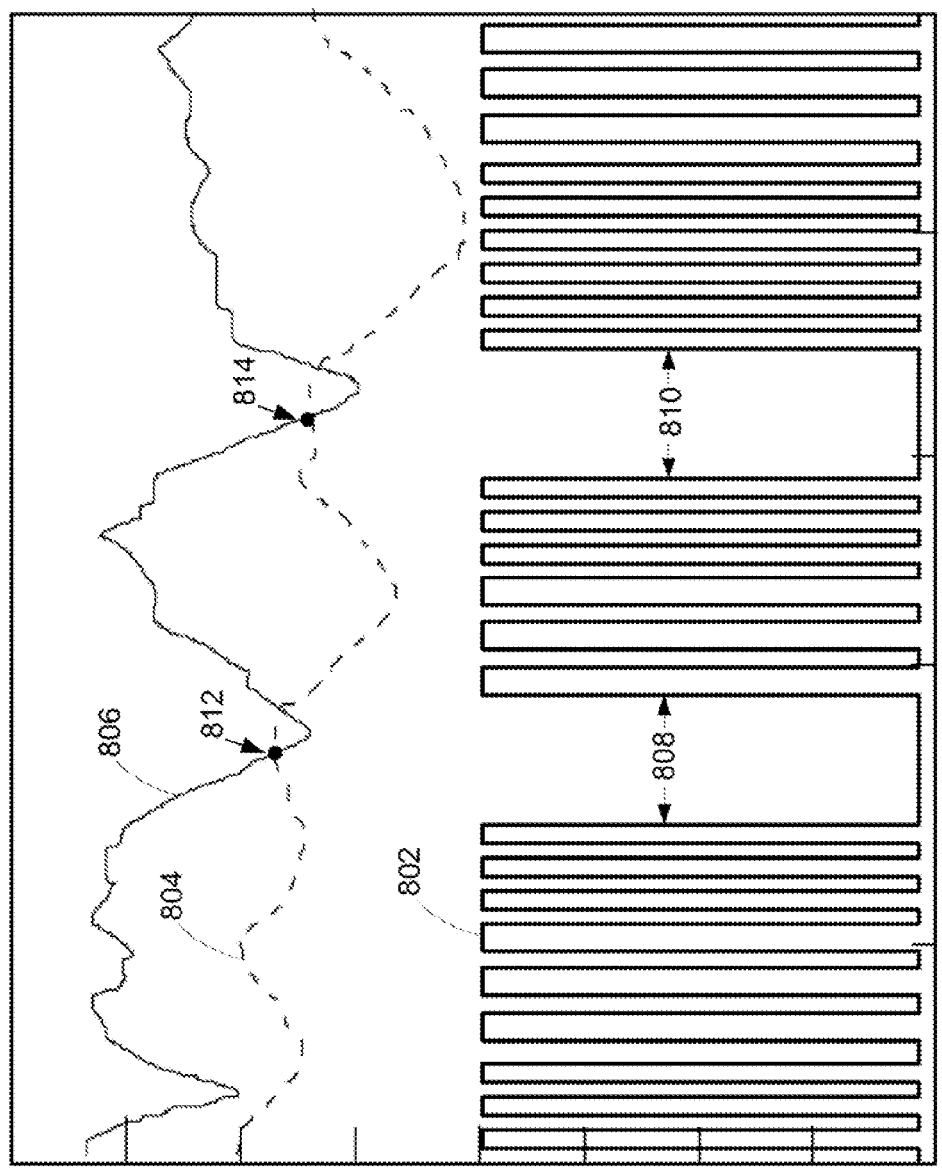
FIG. 8 shows illustrative signals used in connection with detecting held breath events in accordance with some embodiments of the present disclosure.

FIG. 8 shows an illustrative square wave representation of a respiration signal 802, threshold signal 804, and average morphology signal 806 associated with a respiration morphology signal in accordance with some embodiments of the present disclosure. Respiration signal 802 is a square wave representation of respiration over time, with each square wave cycle corresponding to a breath. Held breath portions 808 and 810 of the square wave demonstrate portions of respiration signal 802 where the patient is having a held breath event. In an embodiment, threshold signal 804 and average signal 806 may be generated for one of a respiration morphology signal in accordance with the present disclosure (e.g., based on a down respiration morphology signal). As is depicted in FIG. 8, because threshold signal 804 is based on an extended sample of data (e.g., 10 5-second windows of received data), threshold signal 804 has a delayed response to held breath events, such that threshold signal 804 experiences a sharp decrease at a delay from the onset held breath events 808 and 810. Because average signal 806 is based on a smaller sample of data (e.g., 20 seconds), the average signal 804 responds quicker to held breath events than threshold signal 804, such that average signal 806 experiences a sharp decrease at a lesser delay from the onset of held breath events 808 and 810. At points 812 and 814, the value of average signal 806 may fall below the value of threshold signal 804. As is described with respect to step 612 below, the excursion of average signal 806 below threshold 804 may be used to identify a held breath event.

Referring back to FIG. 6, at step 612, monitor 10 may identify a held breath event based on the comparison of the threshold values to the respective average values. Although it will be understood that a comparison may be performed for any number of the respiration morphology signals, in an embodiment, the comparison may be performed for the threshold and average values associated with each of the down, kurtosis, DSD, b/a ratio, frequency modulation, pulse amplitude, and pulse amplitude morphology signals.

In some embodiments, a held breath event may be identified when a certain minimum number of the morphology signals fall below their respective thresholds. Although any suitable minimum number may be used in accordance with the present disclosure, in an embodiment a held breath event may be identified when a majority of the average signal values fall below the threshold signal values (e.g., 4 of 7 of the respiration morphology signals). In some embodiments, the respiration morphology signals may be assigned differing weights for identifying a held breath event. For example, in some embodiments, each of the respiration morphology signals may be assigned a weighting value, and if the associated average value falls below the threshold value, the weighting value associated with the respiration morphology signal may be added to a total weighting value. If the total weighting value exceeds an overall weighting threshold, monitor 10 may identify a held breath event.

In some embodiments, a held breath event may be identified based on a trained neural network. Although it will be understood that a trained neural network may be configured to identify a held breath event in any manner, in an embodiment, the neural network may be trained based on training data and weights may be assigned to nodes associated with each of the respiration morphology signals. Each node may then assert a node value associated with the assigned weight (e.g., based on the degree to which the average signal falls below the threshold signal) and the node values may be combined (e.g., added) and compared to threshold to determine whether a held breath event has been identified.

Once a held breath event has been initially identified, it may be desired to modify the comparison procedure. Although the comparison procedure may be modified in any suitable manner, in some embodiments, the comparison procedure may be modified by adjusting the threshold, for example, by fixing the threshold at the value at which the average fell below the threshold. In some embodiments, this may retain the held breath indication longer as the threshold value will no longer fall based on the held breath event. After a determination has been made as to whether a held breath event has occurred, processing may continue to step 614.

At step 614, monitor 10 may provide an indication of a held breath event based on the determination at step 612.

Although it will be understood that monitor 10 may provide an indication of a held breath event in any suitable manner, in an embodiment, monitor 10 may stop posting a respiration rate value, provide a visual indication, provide an audible indication, provide a transmitted indication, provide any other suitable indication or response, or any combination thereof.

Although it will be understood that monitor 10 may stop posting respiration rate values in any suitable manner (e.g., immediately upon the identification of a held breath event), in some embodiments, monitor 10 may stop posting respiration rate based on how long the held breath event has persisted. In some embodiments, if a held breath event may has occurred for longer than a threshold duration, monitor 10 may cease posting of respiration rate values. In some embodiments, monitor 10 may have a number of criteria under which the respiration rate may not be posted (e.g., a weak respiration signal, patient speech interfering with the measurement of respiration, etc.). In some embodiments, an indication of a held breath event may be combined with these other criteria, such that if the total duration of all of the events exceeds a threshold, a respiration rate value may not be posted by monitor 10.

In some embodiments, if a respiration rate age is being used to keep track of a confidence of a calculated respiration rate (e.g., representing the average of the age of physiological data being used to calculate respiration rate), then when a held breath event is detected, monitoring system 10 may cause the respiration rate age to be increased as indication of lower confidence in the calculated respiration rate. If the respiration rate age is caused to exceed a posting thresholding, then this may cause the monitoring system 10 to stop posting a respiration rate.

In some embodiments, for relatively long held breath events, a calculated value of oxygen saturation may be used to determine whether to continue posting a respiration rate value. For example, if a held breath event is detected, and the oxygen saturation is decreasing, monitoring system 10 may cease posting respiration rate until the oxygen saturation begins to rise.

It may also be desired to provide an indication of a held breath indication, such as a visual indication, audible indication, or transmitted indication. Although it will be understood that a visual indication may be provided in any suitable manner, in some embodiments, a visual indication may be provided on display 20 as an icon, text, intermittent flashing, changes to display color, any other suitable visual indication of an indication, or any combination thereof.

Although it will be understood that an audible indication may be provided in any suitable manner, in some embodiments, an audible indication may be provided by speaker 22 as a spoken message, indication sound, any other suitable audible indication of an indication, or any combination thereof.

Although it will be understood that a transmitted indication message may be provided in any suitable manner, in some embodiments, a transmitted indication message may be provided by data output 84 to any suitable receiving device such as a central nurse station, smart phone, computing unit, medical pager, medical database, any other suitable receiving device, or any combination thereof.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A computer-implemented method comprising:
   receiving a photoplethysmograph (PPG) signal;
   posting, using processing circuitry, a respiration rate value;
   generating, using the processing circuitry, one or more types of respiration morphology signals based on the PPG signal;
   calculating, using the processing circuitry, a threshold value for each of the one or more respiration morphology signals;
   comparing, using the processing circuitry, data indicative of each respiration morphology signal to a respective one of the threshold values;
   identifying, using the processing circuitry, a held breath event based at least on the comparing; and
   suspending, using the processing circuitry, the posting of a respiration rate value when the held breath event is identified.

2. The method of claim 1, wherein the one or more respiration morphology signals are selected from the group consisting of a down signal, a kurtosis signal, a second derivative signal, a b/a ratio signal, an amplitude signal, an amplitude modulation signal, a frequency modulation signal, and any combination thereof.

3. The method of claim 1, wherein the data indicative of each respiration morphology signal comprises an average of each respiration morphology signal over a predetermined period of time.

4. The method of claim 1, wherein calculating a threshold value comprises determining a mean absolute deviation value for each of the one or more respiration morphology signals.

5. The method of claim 4, wherein calculating a threshold value comprises:
   for each of the one or more respiration morphology signals, determining a plurality of mean absolute deviation values for a respective plurality of time windows; and
   for each of the one or more respiration morphology signals, averaging the mean absolute deviation values of the plurality of time windows.

6. The method of claim 1, further comprising:
   calculating an oxygen saturation from the PPG signal; and
   continuing to suspend the posting until the oxygen saturation is increasing.

7. A system comprising:
   an input for receiving a photoplethysmograph (PPG) signal; and
   processing circuitry configured for:
      posting a respiration rate value;
      generating one or more types of respiration morphology signals based on the PPG signal,
      calculating a threshold value for each of the one or more respiration morphology signals,
      comparing data indicative of each respiration morphology signal to a respective one of the threshold values,
      identifying a held breath event based at least on the comparing; and
      suspending the posting of a respiration rate value when the held breath event is identified.

8. The system of claim 7, wherein the one or more respiration morphology signals are selected from the group consisting of a down signal, a kurtosis signal, a second derivative signal, a b/a ratio signal, an amplitude signal, an amplitude modulation signal, a frequency modulation signal, and any combination thereof.

9. The system of claim 7, wherein the data indicative of each respiration morphology signal comprises an average of each respiration morphology signal over a predetermined period of time.

10. The system of claim 7, wherein the processing circuitry is further configured for determining a mean absolute deviation value for each of the one or more respiration morphology signals.

11. The system of claim 10, wherein the processing circuitry is further configured for:
for each of the one or more respiration morphology signals, determining a plurality of mean absolute deviation values for a respective plurality of time windows; and
for each of the one or more respiration morphology signals, averaging the mean absolute deviation values of the plurality of time windows.

12. The system of claim 7, wherein the processing circuitry is further configured for:
calculating an oxygen saturation from the PPG signal; and
continuing to suspend the posting until the oxygen saturation is increasing.

13. A non-transitory computer readable medium comprising instructions stored therein for performing the method comprising:
receiving a photoplethysmograph (PPG) signal;
posting a respiration rate value;
generating one or more types of respiration morphology signals based on the PPG signal;
calculating a threshold value for each of the one or more respiration morphology signals;
comparing data indicative of each respiration morphology signal to a respective one of the threshold values;
identifying a held breath event based at least on the comparing; and
suspending the posting of a respiration rate value when the held breath event is identified.

14. The computer readable medium of claim 13, wherein the one or more respiration morphology signals are selected from the group consisting of a down signal, a kurtosis signal, a second derivative signal, a b/a ratio signal, an amplitude signal, an amplitude modulation signal, a frequency modulation signal, and any combination thereof.

15. The computer readable medium of claim 13, wherein the data indicative of each respiration morphology signal comprises an average of each respiration morphology signal over a predetermined period of time.

16. The computer readable medium of claim 13, wherein calculating a threshold value comprises determining a mean absolute deviation value for each of the one or more respiration morphology signals.

17. The computer readable medium of claim 16, wherein calculating a threshold value comprises:
for each of the one or more respiration morphology signals, determining a plurality of mean absolute deviation values for a respective plurality of time windows; and
for each of the one or more respiration morphology signals, averaging the mean absolute deviation values of the plurality of time windows.

* * * * *